(12) United States Patent
Hattori (10) Patent No.: US 8,928,884 B2
(45) Date of Patent: Jan. 6, 2015

(54) VALIDATION METHOD FOR AUTOMATED ANALYZERS

(75) Inventor: Akira Hattori, Abiko (JP)

(73) Assignee: Uniflex Company, Ltd. (JP)

( * ) Notice: Subject to any disclaimer, the term of this patent is extended or adjusted under 35 U.S.C. 154(b) by 221 days.

(21) Appl. No.: 13/439,861

(22) Filed: Apr. 5, 2012

(65) Prior Publication Data

US 2012/0257201 A1  Oct. 11, 2012

(30) Foreign Application Priority Data

Apr. 8, 2011   (JP) .................. 2011-086354

(51) Int. Cl.
| | | |
|---|---|---|
| *G01N 21/55* | (2014.01) | |
| *G01N 21/59* | (2006.01) | |
| *G01N 35/00* | (2006.01) | |
| *G01N 35/10* | (2006.01) | |

(52) U.S. Cl.
CPC .......... *G01N 21/59* (2013.01); *G01N 35/00623* (2013.01); *G01N 35/1016* (2013.01)

USPC ................ 356/436; 356/128; 356/445; 435/2

(58) Field of Classification Search
CPC .............. G01N 21/8507; G01N 21/31; G01N 21/0303; G01N 21/59; G01N 21/05
USPC ......................................... 356/436, 445, 128
See application file for complete search history.

(56) References Cited

U.S. PATENT DOCUMENTS

| | | | |
|---|---|---|---|
| 2004/0156748 A1* | 8/2004 | Yamakawa et al. ............. 422/64 |
| 2006/0097155 A1* | 5/2006 | Adachi et al. ................. 250/288 |
| 2006/0166373 A1* | 7/2006 | Enoki et al. ................... 436/180 |
| 2007/0264156 A1* | 11/2007 | Yamakawa et al. ............. 422/63 |
| 2011/0110822 A1* | 5/2011 | Adachi et al. ............. 422/82.09 |

* cited by examiner

Primary Examiner — Tarifur Chowdhury
Assistant Examiner — Isiaka Akanbi
(74) Attorney, Agent, or Firm — Horizon IP Pte Ltd (57) ABSTRACT

Method for validating the accuracy of automated analyzers by performing an improved dye method procedure that uses at least first and second dye solutions in combination with gravimetric measurement of selected test solutions.

14 Claims, 5 Drawing Sheets

VALIDATION METHOD FOR AUTOMATED ANALYZERS

BACKGROUND

Automated analyzers, including clinical biochemistry analyzers and other laboratory devices, have been conventionally used for many years. For example, automated clinical biochemistry analyzers are used to perform clinical testing on blood samples. These devices are required to produce results that are validated, and they must calibrated, i.e., re-validated, on a regular basis.

Such analyzers have been calibrated using "standards" that are composed of the chemical substances present in test serums. However, the problems of accuracy of the calibration can arise, especially in terms of determining absolute values.

A method for improving the accuracy of the calibration can be accomplished by determining the differences between large numbers of test results using standards performed independently through blind studies conducted by several groups. Although this technique can be used universally, it is still inadequate for use as a method for confirming accuracy, because it is burdensome and time consuming.

In recent years, the certified accuracy of verification systems and devices has been determined by using analysis results obtained with a standard as true values based on a theoretical system for establishing the authenticity of world standards, and then determining accuracy by using trueness with respect thereto as a requirement for certification, and it is effective to realize validation techniques that coincide with these certification requirements.

In contrast, a validation technique has been previously proposed that improves calibration accuracy by reducing the effect of evaporation by dispensing an amount of liquid targeted for automated analysis (for example, 1 μl to 1000 μl) as determined according to a standard validation method from a liquid targeted for testing, and validating based on a dye method.

Validation techniques using dye methods consist of placing a prescribed amount of a reference solution containing a first dye component that absorbs light of a first wavelength in an absorbance detection container, measuring the optical absorbance of that wavelength component, placing a detection solution containing a second dye component that absorbs light of a second wavelength in the reference solution, and then measuring the optical absorbance of that wavelength component.

Since a comparison of the optical absorbance of the reference solution and the optical absorbance of the detection solution measured in this manner yields a value corresponding to the amount of the detection liquid, the amount of the detection liquid can be validated based on the amount of the reference liquid (based on the specifications of international standard—ISO8655-part 7).

Validation accuracy can be established for the elements used to determine accuracy of blood analysis results obtained by this dye method by firstly validating the light path length of the cell used for optical analyses, secondly validating the accuracy of dispensing of reaction reagents, thirdly validating the dispensing accuracy of biological specimens (blood), and fourthly validating high-temperature accuracy of the reaction layer.

SUMMARY

The embodiments generally relate to methods for validating and/or calibrating with a high degree of accuracy automated analyzers having liquid dispensers. The present methods for validating the accuracy of automated analyzers are directed to performing an improved dye method validation procedure that uses at least a first dye solution and second dye solution in a target test liquid, measuring at the weight of the second dye solution, performing a first and second optical analysis on the target test liquid, and performing a computational analysis that determines any deviation between and among the first and second optical analyses and the weight measurement for the second dye solution.

In one embodiment of the present method includes the steps of designating as a validation target an automated analyzer that sequentially carries out automated analyses by dispensing an automated analysis target liquid into a plurality of optical analysis cells by an analysis target liquid filling unit and sequentially filling a first dye solution dispensed from a first liquid holding unit into the plurality of optical analysis cells by using the analysis target liquid filling unit. Then, dispensing a second dye solution from a second liquid holding unit by using a diluent dispensing pipetter, and weighing, on the basis of a gravimetric method, a total weight of the diluent dispensing pipetter with the second dye solution using a diluent weighing unit, and pipetting the second dye solution into the optical analysis cells filled with the first dye solution. Measuring a target liquid in the optical analysis cells comprising the first and second dye solutions by an optical absorbance detection unit, based on a dye method, in order to determine the amount of liquid of the first dye solution as a target liquid volume measurement result, weighing, based on the gravimetric method, the diluent dispensing pipetter after pipetting the second dye solution by a pipetter weighing unit, and transferring the target liquid from the optical analysis cells to a reference value measurement unit by using a transfer pipetter and measuring, based on the dye method, to determine by an second optical absorbance detection unit the amount of the first dye solution as a reference liquid volume measurement result. Finally, validating the dispensing accuracy of the analysis target liquid dispensing unit of the automated analyzer by computing any deviation between and among the reference liquid volume measurement result and the target liquid volume measurement result and the measurement results of the pipetter weighing unit and the diluent weighing unit determined based on the gravimetric method.

In another embodiment of the present method includes the steps of designating as a validation target an automated analyzer that sequentially carries out automated analyses by dispensing an automated analysis target liquid into a plurality of optical analysis cells by a first and second analysis target liquid filling units, and sequentially filling a first dye solution into the plurality of optical analysis cells by dispensing from a first liquid holding unit by using the first analysis target liquid filling unit. Then, dispensing a second dye solution from a second liquid holding unit by using a diluent dispensing pipette, and weighing the diluent dispensing pipetter with the second dye solution using a diluent weighing unit, and pipetting the second dye solution into the optical analysis cells filled with the first dye solution. In addition, placing a third dye solution into the optical analysis cells containing the first and second dye solutions, dispensed from a third liquid holding unit, using the second analysis target liquid filling unit. Measuring a target liquid in the optical analysis cells comprising the first, second and third dye solutions by an optical absorbance detection unit, based on a dye method, to determine an amount of the first dye solution as a target liquid volume measurement result, and weighing the diluent dispensing pipetter after pipetting the second dye solution by a pipetter weighing unit, and transferring the target liquid from the optical analysis cells to a reference value measurement unit by using a transfer pipetter and measuring, based on the dye method, to determine by an second optical absorbance detection unit the amount of the first dye solution as a reference liquid volume measurement result. Finally, validating the dispensing accuracy of the analysis target liquid dispensing unit of the automated analyzer by computing any deviation between and among the reference liquid volume measurement result and the target liquid volume measurement result and the measurement results of the pipetter weighing unit and the diluent weighing unit determined based on the gravimetric method.

According to the present method, the accuracy of validation results for an automated analyzer can be improved by determining the amount of a validation target liquid based on measurement of the amount of a reference liquid with respect to the amount of the validation target liquid based on measurement of a target liquid by a dye method using first and second retroactive dye solutions, using a target value measurement result according to a gravimetric method.

These and other objects, along with advantages and features of the present invention herein disclosed, will become apparent through reference to the following description and the accompanying drawings. Furthermore, it is understood that the features of the various embodiments described herein are not mutually exclusive and can exist in various combinations and permutations.

DESCRIPTION

Figure 1:
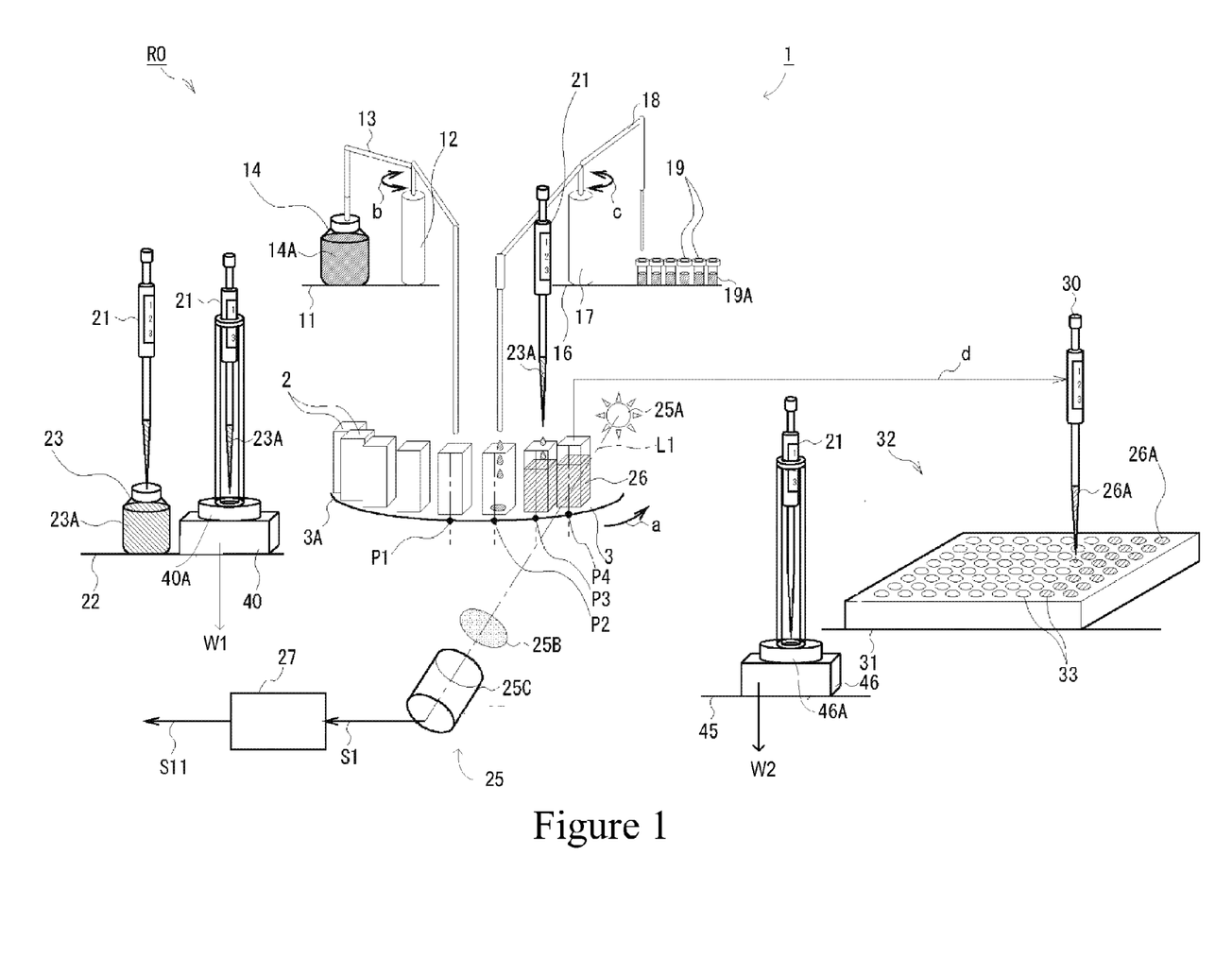
FIG. 1 is a schematic system diagram showing an embodiment of the present method.

A clinical biochemistry automated analyzer RO, which is the validation target of the automated analyzer validation device 1, holds sample blood serving as an analysis target in sample cups 19 on a sample rack 16, dispenses a small prescribed amount of the sample blood from each of the sample cups 19 with a dispensing tube 18 that rotates in the direction indicated by arrow c in a sample filling unit 17 that composes a first analysis target filling unit, and fills the sample blood into optical analysis cells 2.

In addition, the clinical biochemistry automated analyzer RO holds a sample reagent, which develops a red color by reacting with a serum component to be analyzed at normal temperature, in a reagent bottle 14 on a reagent rack 11, dispenses a small prescribed amount of the reagent with a dispensing tube 13 that rotates in the direction indicated by arrow b in a reagent filling unit 12 that composes a second analysis target filling unit, and fills the reagent into the optical analysis cells 2.

A plurality of the optical analysis cells 2 are sequentially arranged along a peripheral edge 3A of a turntable 3 that rotates intermittently in the direction indicated by arrow a, and as a result thereof, when the dispensing tubes 18 and 13 of the sample filling unit 17 and the reagent filling unit 12 have rotated to a prescribed filling position, each of the optical analysis cells 2 is sequentially filled with the sample blood and the coloring reagent.

Thus, the clinical biochemistry automated analyzer RO serving as the validation target of the automated analyzer validation device 1 is able to automatically analyze sample blood dispensed from the plurality of sample cups 19A based on a chemical component contained in the serum thereof reacting in the optical analysis cells 2.

In FIG. 1, during a typical automated analysis operation, the automatic analyzer validation device 1 fills a dye solution having a first dye (red) serving as the sample liquid 19A into the sample cups 19 serving as liquid retention portions that hold the sample blood when validating the clinical biochemistry automated analyzer RO serving as the validation target.

As a result, the automated analyzer validation device 1 in the case of FIG. 1 validates the amount dispensed by the sample dispensing unit 17.

In the automated analyzer validation device 1, when the turntable 3 of the clinical biochemistry automated analyzer RO has been rotated intermittently in the direction indicated by arrow a, the optical analysis cells 2 are sequentially positioned at a reagent filling position P1, a sample filling position P2, a diluent filling position P3 and a target measuring position P4.

When an optical analysis cell 2 has been positioned at the sample filling position P2, the automated analyzer validation device 1 dispenses a prescribed amount of the sample liquid 19A from the plurality of sample cups 19 with the dispensing tube 18 of the sample filling unit 17 provided on the sample rack 16 and fills the sample liquid 19A into the optical analysis cell 2.

Incidentally, the amount dispensed by the sample filling unit 17 at this time is equal to the amount of sample blood dispensed when the clinical biochemistry automated analyzer RO performs automated analysis.

The sample filling unit 17 aspirates the sample liquid 19A from the plurality of sample cups 19 arranged in a row on the sample rack 16, and as indicated by arrow c, rotates the dispensing tube 18 from the position of the sample cups 19 to the sample filling position P2 and fills the aspirated sample liquid 19A into the optical analysis cells 2 followed by returning the dispensing tube 18 to its original position of the sample cups 19.

In the case of this embodiment, a first dye solution is used for the sample liquid 19A that demonstrates the optical characteristic of absorbing an optical component having a wavelength of 520 nm due to a first red dye.

This first dye solution is a dye solution that contains a known error with respect to the red dye solution defined in the previously mentioned international standard ISO8655-7, and is referred to as a "retroactive first dye solution" since this characteristic can be made to be retroactive to the above-mentioned standard in consideration of this "known error".

The automated analyzer validation device 1 is made to fill a diluent 23A from the diluent dispensing pipetter 21 when the optical analysis cells 2 have been positioned at the diluent filling position P3.

Dispensing work performed by the diluent dispensing pipetter 21 is carried out manually by an analysis technician of the clinical biochemistry automated analyzer RO.

During this dispensing work, a dispensing technician operates the diluent dispensing pipetter 21 and first aspirates a prescribed amount of a diluent 23A from a diluent bottle 23 serving as a liquid holding portion arranged on a diluent rack 22.

In the case of this embodiment, a second dye solution is used for the diluent 23A that demonstrates the optical characteristic of absorbing an optical component having a wavelength of 730 nm due to a second blue dye.

This second dye solution is a dye solution that contains a known error with respect to the blue dye solution defined in the previously mentioned international standard ISO8655-7, and is referred to as a "retroactive second dye solution" since this characteristic can be made to be retroactive to the abovementioned standard in consideration of this "known error".

When an optical analysis cell 2 has reached the target measuring position P4 as a result of rotation of the turntable 3, the automated analyzer validation device 1 detects the optical absorbance of a measurement target liquid 26 contained in the optical analysis cell 2 with an optical absorbance detection unit 25, and transmits an optical absorbance detection signal S1 to a target measurement result processing unit 27 having the configuration of a microcomputer.

In this embodiment, the optical absorbance detection unit 25 comprises a detecting light L1 emitted from a white light source 25A being passed through the optical analysis cell 2, the optical absorbance detection unit 25 extracts a light component of a prescribed measurement wavelength range with a filter 25B and allows the light to enter a photoelectric converter 25C.

As a result, the detecting light L1 enters the filter 25B after the optical component of a wavelength corresponding to the optical absorbance characteristics of the dye present in a measurement target liquid 26 has been absorbed as a result of passing through the measurement target liquid 26.

In this embodiment, the measurement target liquid 26 contains a 520 nm wavelength component possessed by the red dye solution 19A filled into the optical analysis cells 2 at the sample filling position P2, and a 730 nm wavelength component possessed by the blue dye solution 23A filled at the diluent filling position P3.

Figure 2:
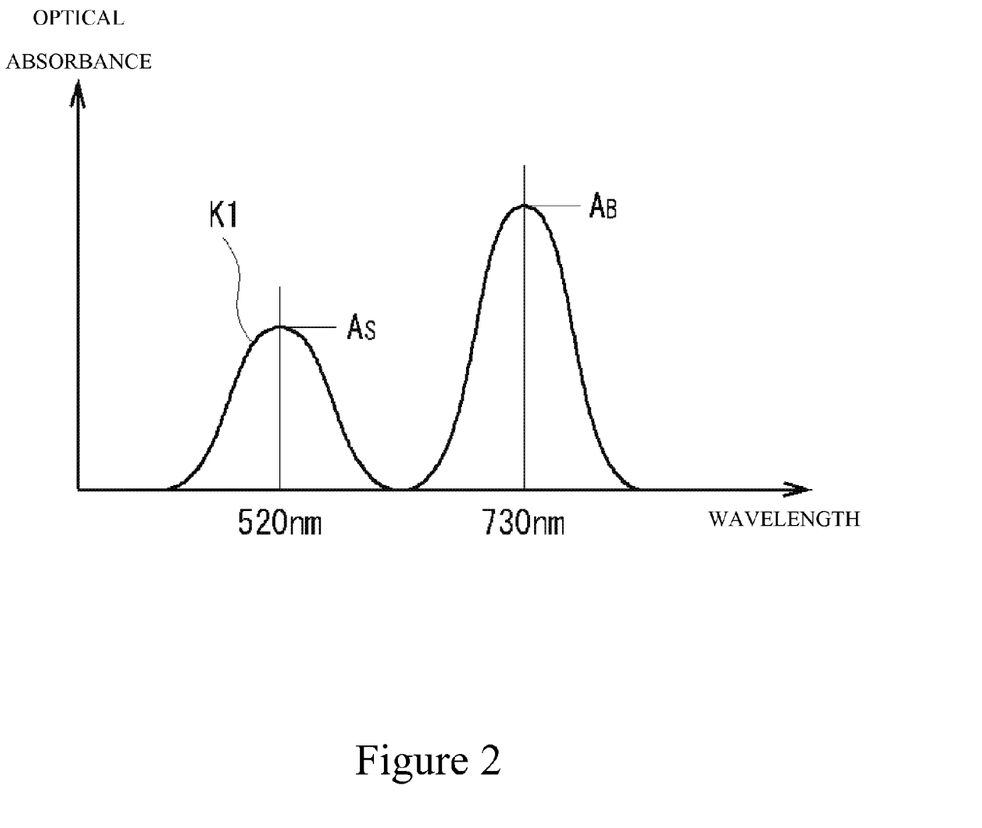
FIG. 2 is a typical absorbance curve results of the present method.

Thus, the wavelength components of the measurement target liquid 26 in the optical analysis cells 2 at the target measuring position P4 are absorbed in accordance with the optical absorbance curve K1 shown in FIG. 2 for the 520 nm and 730 nm wavelength components.

As a result, in the optical absorbance detection unit 25, by calculating the following by the target measurement result processing unit 27 based on the ratio of the optical absorbance of the two wavelength components:

$$V_S = V_B \left[ \frac{\frac{A_S}{A_B}}{K - \frac{A_S}{A_B}} \right] \quad (1)$$

$V_S$=volume of red dye solution
$V_B$=volume of blue dye solution
$A_S$=optical absorbance of red dye solution (520 nm)
$A_B$=optical absorbance of blue dye solution (730 nm)
K=correction value determined at time of shipment from factory the dispensed amount of the test liquid 19A in the form of the red dye solution can be determined based on the dispensed amount of the diluent 23A in the form of the blue dye solution.

Here, formula (1) is specified as a liquid volume measurement method, based on the dye method according to international standard ISO8655-7, and indicates that the amount of the sample liquid 19A dispensed by the dispensing tube 18, namely the volume $V_S$ of the sample liquid 19A, can be determined as a value obtained by multiplying the ratio of the optical absorbance $A_S$ of the sample liquid 19A in the form of the red dye solution to the optical absorbance $A_B$ of the diluent 23A by the dispensed amount of the diluent in the form of the blue dye solution by the diluent dispensing pipetter 21, namely the volume $V_B$ of the diluent 23A.

In addition, since the ratio of the optical absorbance $A_S$ of the sample liquid 19A to the optical absorbance $A_B$ of the diluent 23A represents the degree of dilution of the sample liquid 19A relative to the diluent 23A, this indicates that the injection volume $V_S$ of the sample liquid 19A can be determined as the ratio of the injection volume of the sample liquid 19A to the volume of the diluent 23A contained in the optical analysis cells 2.

In this manner, the optical absorbance detection unit 25 and the target measurement result processing unit 27 compose a target liquid volume measurement unit for the measurement target liquid 26 in the optical analysis cells 2 at the target measuring position P4.

As indicated by arrow d, the entire volume of the measurement target liquid 26 filled into the optical analysis cells 2 at the target measuring position P4 is removed as a measurement target transfer liquid 26A by a dispensing technician using the transfer pipetter 30, and transferred to a reference value measurement microplate 32 on a reference value rack 31.

The entire volume of the measurement target liquid 26 is aspirated from the optical analysis cells 2 with the transfer pipetter 30 during manual work performed by a dispensing technician in the same manner as previously described with respect to the diluent dispensing pipetter 21, and the measurement target liquid 26 is transferred to one of a plurality of retention grooves 33 provided in the reference value measurement microplate 32.

In addition to having the configuration previously described, the validation device 1 is provided with a balance 40A that composes the diluent weighing unit 40 on the diluent rack 22.

The balance 40A of the diluent weighing unit 40 weighs the total weight of the diluent dispensing pipetter 21 and the diluent 23A contained therein as a result of a dispensing technician dispensing the diluent 23A from the diluent bottle 23 using the diluent dispensing pipetter 21, and placing on the balance 40A that composes the diluent weighing unit 40.

In addition to recording the result W1 of weighing in the diluent weighing unit 40, the dispensing technician fills the diluent 23A by transporting the diluent dispensing pipetter 21 retaining the dispensing liquid 23A to the optical analysis cells 2 at the diluent filling position P3.

Following this dispensing work, an operator executing diluent operation places the diluent dispensing pipetter 21 that has currently been used on a balance 46A that composes the pipetter weighing unit 46 provided on a pipetter rack 45 for a weight result W2. It is within the scope of the present method to use weighing unit 46 to obtain this weight measurement for the empty pipette 21.

At this time, the pipetter weighing unit 46 determines the weight of the diluent dispensing pipetter 21 per se after having emptied the diluent 23A into optical analysis cell 2, and the dispensing technician records the result of that weighing.

In this manner, the weight of the diluent 23A filled into the optical analysis cells 2 by the dispensing technician at the diluent filling position P3, and thus the amount of the diluent 23A dispensed by the diluent dispensing pipetter 21, can be determined by a gravimetric method by comparing the weighing result obtained from the diluent weighing unit 40 and the weighing result obtained from the pipetter weighing unit 46.

Figure 3:
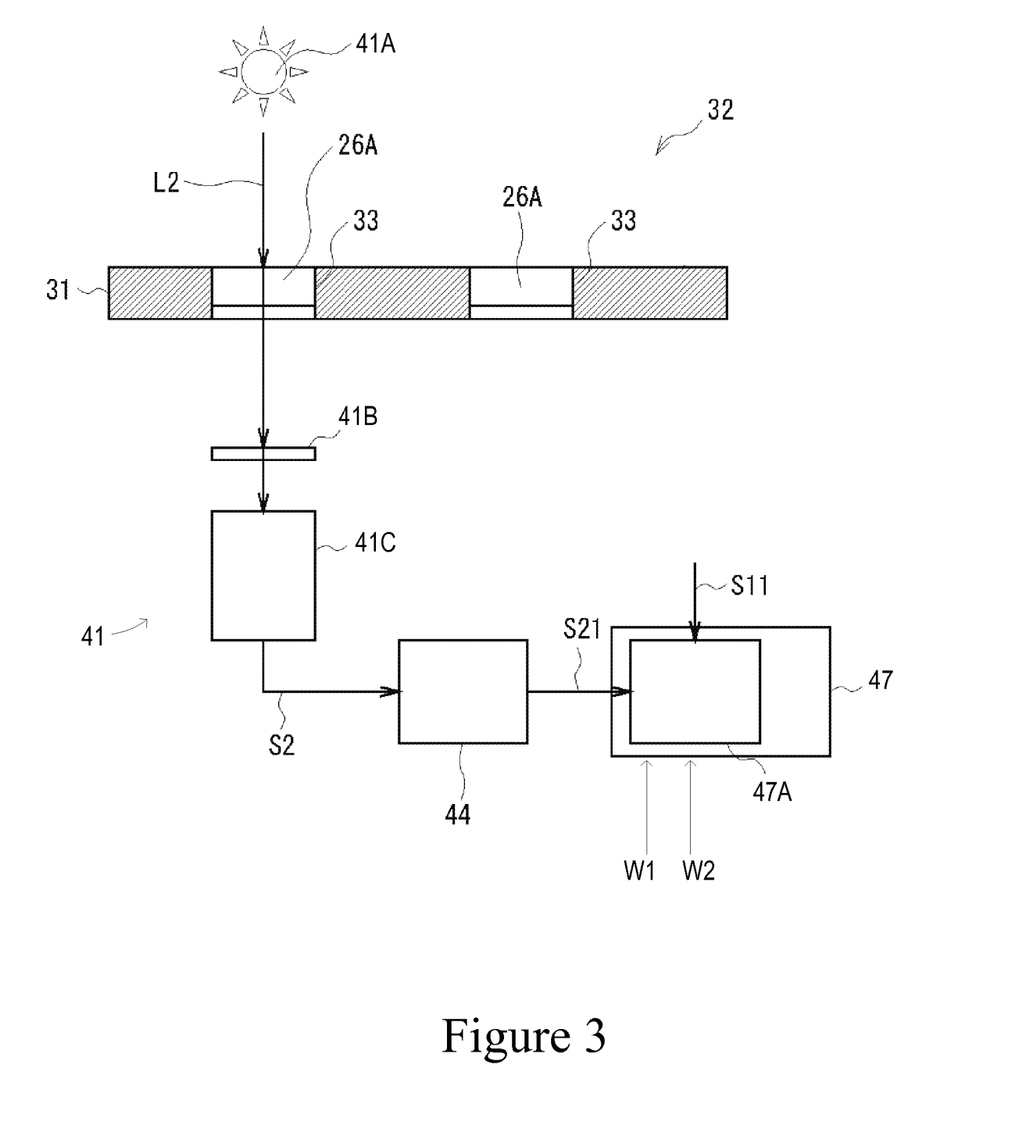
FIG. 3 is a schematic system diagram showing the configuration of the second optical absorbance detection unit and a reference value measurement microplate.

As shown in FIG. 3, a second optical absorbance detection unit 41 is used to measure the amount of the measurement target transfer liquid 26A placed in the retention grooves 33 of the reference value measurement microplate 32 using a dye method as a highly accurate reference value.

The optical absorbance detection unit 41 has a white light source 41A that emits a white light L2, and causes the white light L2 to enter a photoelectric converter 41C with respect to a filter 41B after having passed through the measurement target transfer liquid 26A.

Here, as was previously described with respect to FIG. 2, the measurement target transfer liquid 26A has optical absorbance characteristics such that a blue dye component of a wavelength of 730 nm of the diluent 23 and a red dye component of a wavelength of 520 nm of the sample liquid 19A are absorbed as represented by the optical absorbance curve K1, and the filter 41B extracts light of a wavelength range that includes these dye components followed by the light entering the photoelectric converter 41C.

The photoelectric converter 41C is configured so as to arithmetically process the above-mentioned formula (1) at high accuracy, including known error (thus, making it retroactive), based on the specifications of the previously described international standard ISO8655-7, and as a result, an optical absorbance detection signal S2 obtained from the photoelectric converter 41C is transmitted to a reference measurement result processing unit 44 having the configuration of a microcomputer as a reference value representing the volume of the sample liquid 19A contained in the measurement target transfer liquid 26A at a high level of accuracy that is close to that of the measurement result obtained with a standard equivalent to the device of the aforementioned international standard.

In this manner, the reference measurement result processing unit 44 retains the measurement result of the volume of the sample liquid 19A contained in the measurement target transfer liquid 26A with high accuracy as a reference value.

The optical absorbance detection unit 41 determines measured values for reference values in this manner for the measurement target transfer liquid 26A retained in all of the retention grooves 33 of the reference value measurement microplate 32, and accumulates those measured values in the reference measurement result processing unit 44.

The reference value measurement result accumulated in the reference measurement result processing unit 44 of the reference value judgment unit 32 is transmitted to the dispensing accuracy judgment unit 47A of the validation result processing unit 47 as a reference liquid volume signal S21.

The dispensing accuracy judgment unit 47A determines a difference between the target liquid volume signal S11 obtained from the target measurement result processing unit 27 (FIG. 1) and the reference liquid volume signal S21 obtained from the reference value measurement result processing unit 44, and validation result processing unit 47 confirms the amount dispensed by the diluent dispensing pipetter 21 using a gravimetric method based on the weighing results W1 and W2 of the diluent weighing unit 40 and the pipetter weighing unit 46, respectively, as a validation result that expresses the measuring limit (uncertainty) of the clinical biochemistry automated analyzer RO serving as the validation target.

It is within the scope of the present method to have the target measurement result processing unit 27, the reference value measurement result processing unit 44 and the validation result processing unit 47 be a single microprocessor or computer or be distributed as shown.

Figure 4:
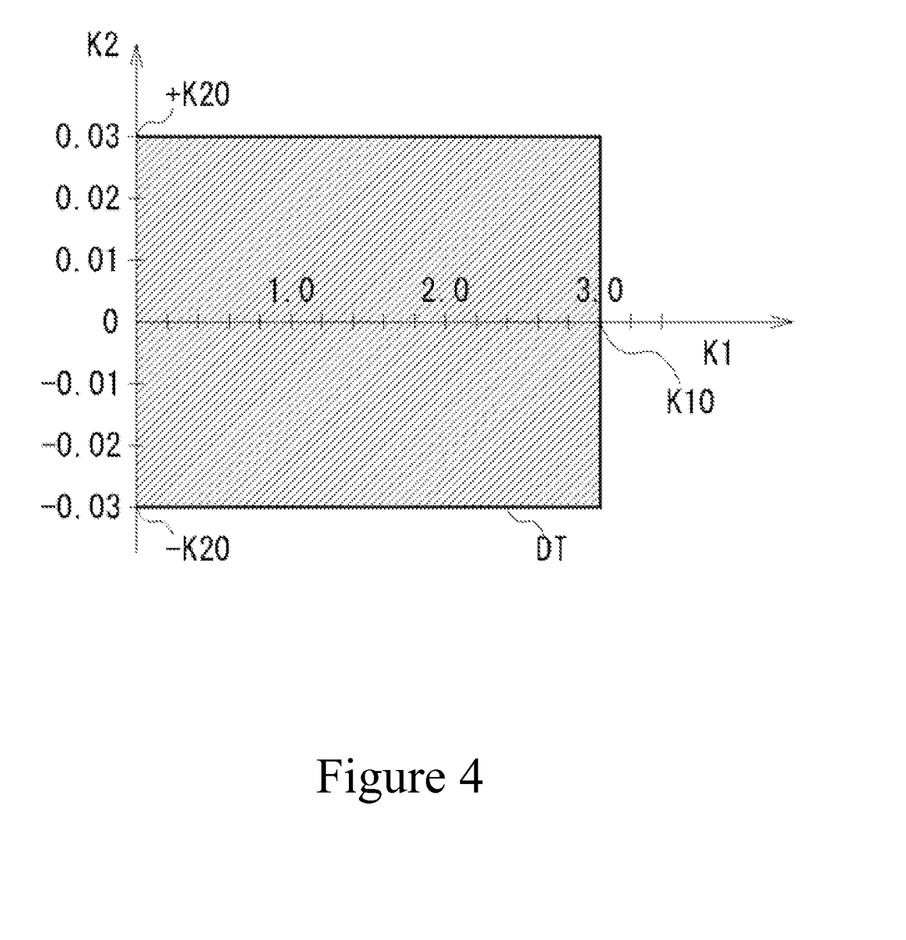
FIG. 4 is a typical graphical representation of the validation/calibration results of the present method.

As shown in FIG. 4, in addition to plotting a coefficient of variation K1 within the range of 0% to 3.0% on the horizontal axis, by further plotting a degree of accuracy K2 within the range of −0.03 to +0.03 on the vertical axis, this validation result can be expressed according to whether or not the dispensing accuracy for the amount of the sample liquid 19A dispensed from the sample cups 19 by the sample filling unit 17 lies within a dispensing accuracy curve DT.

Here, the coefficient of variation K1 represents the degree of variation of the validation result, while the degree of accuracy K2 is equal to 0 when the validated dispensing amount is the true value, and the degree of variation from the true value K2=0 is represented as K2+0.01, +0.02 . . . or −0.01, −0.02 . . .

In this manner, when a validation result is within an area demarcated by the dispensing accuracy curve DT that passes through a target coefficient of variation K1=0 to K=10 and a target degree of accuracy K2=+K20 to −K20, the dispensing accuracy of the automated analyzer serving as the validation target is validated to be within the allowed range.

The method provides an automated analyzer RO is the validation target that sequentially carries out automated analyses by dispensing an automated analysis target liquid 19A into a plurality of optical analysis cells 2 by way of sample filling unit 17. A first dye solution 19A is sequentially filled into the plurality of optical analysis cells 2 dispensing from a first liquid holding unit 19, and together with dispensing a second dye solution 23A from a second liquid holding unit 23 through the use of a diluent dispensing pipetter 21. The total weight of the diluent dispensing pipetter 21 in the dispensing state, i.e., with the dye solution, is obtained, based on a gravimetric method, using a diluent weighing unit 40. The second dye solution 23A is dispensed into the optical analysis cells 2 which is already filled with the first dye solution 19A.

Thereafter, determining the amounts of liquid in the optical analysis cells 2 filled with the first and second dye solutions 19A and 23A by using an optical absorbance detection unit 25 (based on a dye method) to determine a target measured value, weighing the emptied diluent dispensing pipetter 21 (after having been filled with the second dye solution 23A) using a pipetter weighing unit 46, based on a gravimetric method. Transferring the contents of the optical analysis cells 2 filled with the first and second dye solutions 19A and 23A to a reference value measurement microplate 32 using a transfer pipetter 30 and measuring (based on a dye method) using a second optical absorbance detection unit 43 to obtain a reference measured value. Performing a computational analysis using all of the measured results obtained by the present method to validate the dispensing accuracy of the sample filling unit 17 of the automated analyzer RO by determining any deviation between and among the reference measured value and the target measured value determined based on a dye method and the deviation between measurement results of the pipetter weighing unit 46 and the diluent weighing unit 40 determined based on a gravimetric method.

Figure 5:
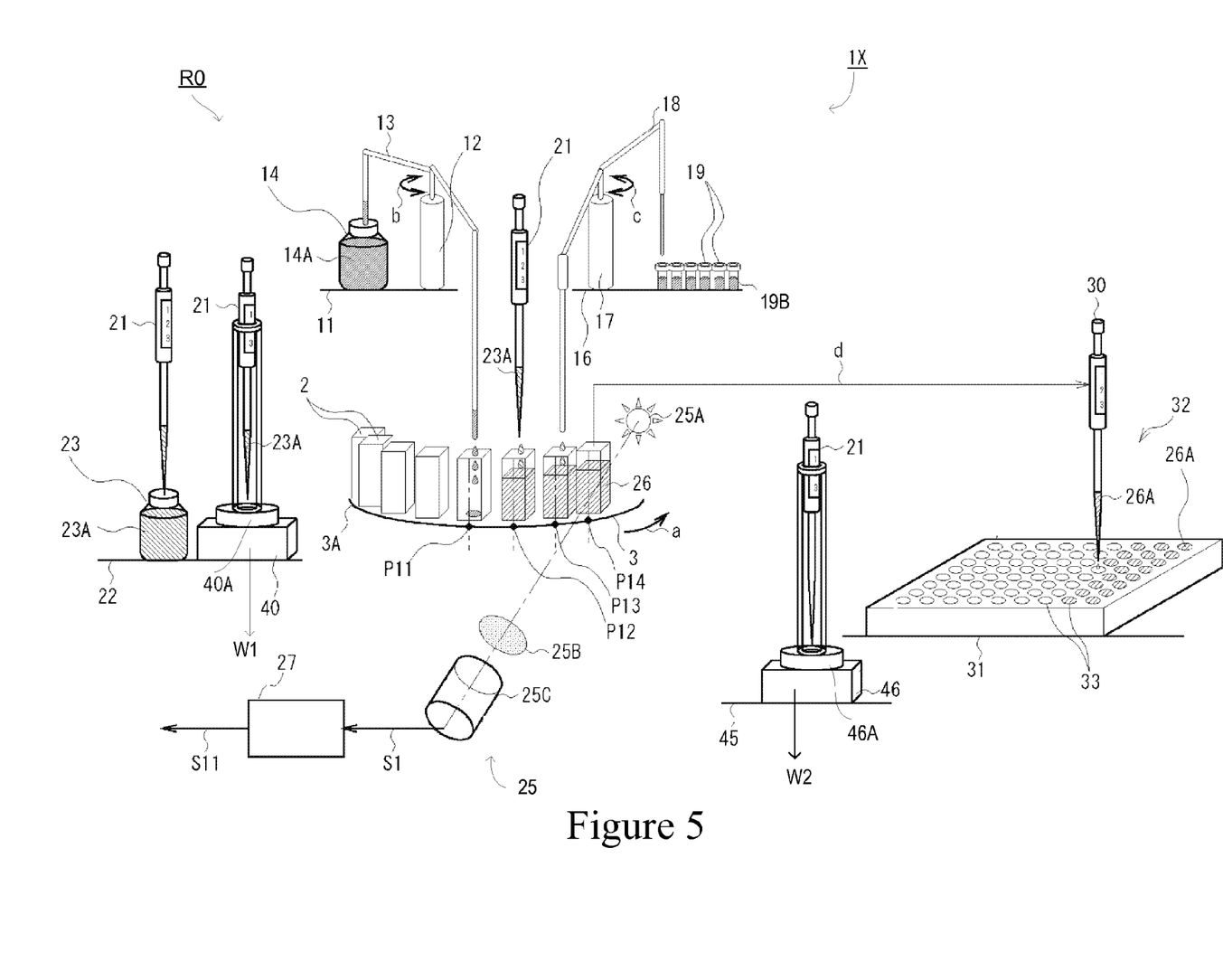
FIG. 5 is a schematic system diagram showing a second embodiment of the present method.

In FIG. 5, another embodiment of the present method, the same reference symbols are used to indicate those elements and features corresponding to FIG. 1.

The automated analyzer validation device 1X of FIG. 5 differs from the automated analyzer validation device 1 of FIG. 1 in that, in contrast to the automated analyzer validation device 1 of FIG. 1 (directed to determining the dispensed amount of the sample liquid 19A that is a red dye solution based on the dispensed amount of the diluent 23A that is blue dye solution using a dye method), the validation device 1X of FIG. 5 determines the dispensed amount of a reagent solution 14A that is a red dye solution based on the dispensed amount of the diluent 23A and the sample liquid 19B that are blue dye solutions.

Namely, in the case of FIG. 5, the reagent solution 14A dispensed from the reagent bottle 14 is filled into optical analysis cells 2 on the turntable 3 by a reagent filling unit 12 at a reagent filling position P11.

In this case, a first dye solution demonstrating the optical characteristic of absorbing an optical component having a wavelength of 520 nm due to the first red dye solution is used for the reagent solution 14A.

Continuing, the diluent 23A manually dispensed from the diluent bottle 23 by a dispensing technician is filled into the optical analysis cells 2 by the diluent dispensing pipetter 21 at a diluent filling position P12.

In this case, a second dye solution demonstrating the optical characteristic of absorbing an optical component having a wavelength of 730 nm due to the second blue dye is used for the diluent 23A.

Here, prior to filling the diluent 23A at the diluent filling position P12, the diluent dispensing pipetter 21 in the state of having dispensed the diluent 23A is placed on the balance 40A that composes the diluent weighing unit 40 and the total weight thereof is weighed.

After having filled the diluent 23A, the diluent dispensing pipetter 21 is placed on the balance 46A that composes the pipetter weighing unit 46 and the weight of the pipetter 21 per se is weighed.

Continuing, the sample liquid 19B dispensed from the sample cups 19 by the sample filling unit 17 is filled into the optical analysis cells 2 at a sample filling position P13.

In this case, a third dye solution demonstrating the optical characteristic of absorbing optical components having a wavelength of 730 nm due to the second blue dye in the same manner as the above-mentioned diluent 23A is used for the sample liquid 19B.

Continuing, the optical absorbance of the measurement target liquid 26 in the optical analysis cells 2 is detected by the optical absorbance detection unit 25 at a measurement target position P14.

Accompanying this, the entire volume of liquid filled into the optical analysis cells 2 is transferred to a reference value judgment pallet 32 of the reference value judgment unit 32 by the transfer pipetter 30 at the target measuring position P14 as indicated by arrow d.

In the configuration of FIG. 5, when an optical analysis cell 2 has been brought to the reagent filling position P11 by the turntable 3, the validation device 1X dispenses a first dye solution in the form of the reagent solution 14A from the reagent bottle 14 with the dispensing tube 13 of the reagent filling unit 12 and fills the optical analysis cell 2.

Continuing, after the second dye solution in the form of the diluent dispensed by the diluent dispensing pipetter 21 from the diluent bottle 23 by a dispensing technician has been filled into the optical analysis cells 2 filled with the reagent solution 23A at the diluent filling position P12, the detection device 1X fills the third dye solution in the form of the sample liquid dispensed from the sample cups 19 by the sample filling unit 17 into the optical analysis cells 2 at the sample filling position P13.

In this manner, as a result of the red first dye solution of the first dye filled at the reagent filling position P11, the blue second dye solution of the second dye filled from the diluent dispensing pipetter 21 at the diluent filling position P12, and the blue third dye solution of the second dye filed by the sample filling unit 17 at the sample filling position P13 being mixed in the optical analysis cells 2, the optical absorbance detection unit 25 detects optical absorbance at the measurement target position P14 by using this mixture as the measurement target liquid 26.

At this time, the optical absorbance detection unit 25 determines the volume of the red reagent solution 14A serving as the first dye based on the ratio between the optical absorbance of the reagent solution 14A serving as the red wavelength component of the first dye and the optical absorbance of the diluent solution 23A and the sample liquid 19B serving as blue wavelength components of the second dye in accordance with the above-mentioned formula (1) using a dye method based on the specifications of ISO8655-7, and accumulates that volume in the target measurement result processing unit 27.

Here, in conjunction with the liquid volume of the second dye (blue), although error occurs in the liquid volume of the first dye (red) in the above-mentioned formula (1) due to the sample liquid 19B having been filled into the diluent 23A, if the amount of the diluent 23A (namely, the second dye solution) that composes the liquid volume of the second dye (blue) is known and the amount of the sample liquid 19B (namely, the third dye solution) is known, then the amount of the reagent solution 14A of the first dye (namely, the first dye solution) can be determined with high accuracy with little effect of evaporation in the dye method.

When this is done, in the case of FIG. 5 as well, in addition to weighing the total weight, including the diluent 23A dispensed from the diluent bottle 23 by the diluent dispensing pipetter 21 in the diluent weighing unit 40, a dispensing technician also weighs the weight of the diluent dispensing pipetter 21 after having filled the diluent 23A at the diluent filling position P12 in the pipetter weighing unit 46.

In this manner, the amount of the diluent 23A dispensed by the diluent dispensing pipetter 21 can be confirmed by a gravimetric method according to the difference between the weighing result of the diluent weighing unit 40 and the weighing result of the pipetter weighing unit 46.

In addition, the dispensed amount of the measurement target transfer liquid 26A transferred to the retaining grooves 33 of the reference value measurement microplate 32 by the transfer pipetter 30 is determined as a highly accurate reference value corresponding to a standard based on the dye method by the reference value judgment microplate 32 of FIG. 3.

This reference value judgment result represents the dispensed amount of the red component contained in the measurement target transfer liquid 26A transferred by the transfer pipetter 30, namely the dispensed amount of the reagent solution 14A of the first dye solution dispensed from the reagent bottle 14 by the reagent filling unit 12, and this is accumulated in the reference value judgment result processing unit 44 of the reference value judgment microplate 32.

In this manner, the validation result processing unit 47 of the reference value judgment microplate 32 is able to determine a dispensing accuracy curve DT as previously described with respect to FIG. 4 by comparing and judging the target liquid volume signal S11 obtained from the target measurement result processing unit 27 and the reference liquid volume signal S21 obtained from the reference value measurement result processing unit 44.

As a result, the validation device 1X of FIG. 5 is able to validate the dispensing accuracy of the reagent filling unit 12 of the clinical biochemistry automated analyzer RO serving as the validation target based on the resulting dispensing accuracy curve DT.

In this manner, the liquid volume of the blue dye component can be measured according to a gravimetric method based on the weighing result of the diluent weighing unit 40 and the weighing result determined by the pipetter weighing unit 46, and this can be confirmed based on a gravimetric method as the liquid volume $V_B$ of the blue dye liquid in the arithmetic processing of the aforementioned formula (1) based on a dye method, thereby making it possible to even more reliably confirm certainty with respect to results of measuring the dispensed amount of the red component.

Incidentally, if the amount of the reagent solution 14A dispensed by the reagent filling unit 12 is determined according to a dye method using the configuration shown in FIG. 5 after having determined the amount of the sample liquid 19B dispensed by the sample filling unit 17 according to a dye method using the validation device 1 having the configuration shown in FIG. 1, validation of the dispensed amount of the sample filling unit 17 used to dispense blood and validation of the dispensed amount of the reagent filling unit 12 used to dispense a coloring reagent, which are both important elements of analysis results in the clinical biochemistry automated analyzer RO, can be carried out with high accuracy.

The method of FIG. 5 provides an automated analyzer RO is the validation target that sequentially carries out automated analyses by respectively dispensing an automated analysis target liquid 14A into a plurality of optical analysis cells 2 by first and second analysis target liquid filling units 12 and 17. A first dye solution 14A is sequentially filled into the plurality of optical analysis cells 2 by dispensing from a first liquid holding unit 14 by using the first analysis target liquid filling unit 12, and together with dispensing a second dye solution 23A from a second liquid holding unit 23 using a diluent dispensing pipetter 21, the total weight of the diluent dispensing pipetter 21 with the second dye solution 23A is weighed by a diluent weighting unit 40, based on a gravimetric method. A third dye solution 19B, which the same dye as the second dye solution 23A, is dispensed into the optical analysis cells 2 filled with the first and second dye solutions 14A and 23A from a sample cup 19 by using the sample filling unit 17.

Measuring the amounts of liquid in the optical analysis cells 2 filled with the first, second and third dye solutions, i.e., 14A, 23A and 19B, respectively, by an optical absorbance detection unit 25 (based on a dye method) in order to determine the amount of the first dye solution 14A as a target value measurement result. Obtaining the weight of the diluent dispensing pipetter 21 after having been filled with the second dye solution 23A by a pipetter weighing unit 46 based on a gravimetric method.

Transferring the entire content from the optical analysis cells 2 filled with the first, second and third dye solutions, i.e., 14A, 23A and 19B, respectively, to a reference value measurement microplate 32 by using a transfer pipetter 30. Based on a dye method, using a second optical absorbance detection unit to determine the amount of the first dye solution 14A as a reference value measurement result. Performing a computational analysis to validate the dispensing accuracy of the analysis target liquid filling unit 12 of the automated analyzer RO, according to any deviation between and among the reference value measurement result and the target value measurement result, determined based on a dye method, and the deviation between the measurement results of the pipetter weighing unit 46 and the diluent weighing unit 40 determined based on a gravimetric method.

Although the above-mentioned embodiments described the application of the present invention to a clinical biochemistry automated analyzer used for hematological testing, the present invention is not limited thereto, but rather can also be applied to a wide range of other clinical biochemistry automated analyzers.

It is also within the scope of the present method to have the manual pipetting of the dye solutions and target liquids performed by a robotic handling device or automated dispensing units to have a fully automated process. In addition, the weighing of the pipette may be performed on a single weighing unit.

The preferred embodiment of the invention is illustrative of the invention rather than limiting of the invention. It is to be understood that revisions and modifications may be made to methods and systems described herein while still providing a manufacturing automation system and an automated method for movement of material that fall within the scope of the included claims. All matters hitherto set forth herein or shown in the accompanying figures are to be interpreted in an illustrative and non limiting sense.

What is claimed is:

1. A method for validating the accuracy of automated analyzers comprising:
    providing a first dye solution which absorbs light of a first wavelength into one of a plurality of optical analysis cells;
    measuring the weight of a second dye solution which absorbs light of a second wavelength which is different from the first wavelength, wherein the weight of the second dye solution is measured based on gravimetric method;
    providing the second dye solution into the optical analysis cell containing the first dye solution, wherein the first and second dye solutions form a target test liquid;
    performing a first optical measurement based on a dye method on the target test liquid contained in the optical analysis cell to obtain an amount of the first dye solution as a first measurement result;
    removing the target test liquid from the optical analysis cell and transferring the same target test liquid into a microplate which is separated and independent from the optical analysis cell;
    performing a second optical measurement based on the dye method on the same target test liquid contained in the microplate to obtain the amount of the first dye solution as a second measurement result; and
    validating the accuracy of the amount of the first dye solution by performing a computational analysis to determine any deviation between and among the first and second measurement results and the weight measurement of the second dye solution.

2. The method of claim 1 wherein removing the target test liquid from the optical analysis cell and transferring the same target test liquid to the microplate are performed prior to performing the second optical measurement.

3. The method of claim 1 comprising providing a third dye solution into the optical analysis cell to form the target test liquid.

4. The method of claim 3 wherein the third dye solution absorbs light of the second wavelength.

5. The method of claim 4 wherein the first dye solution has a red absorption wavelength component, and the second and third dye solutions have a blue absorption wavelength component.

6. The method of claim 3 wherein the third first dye solution is provided into the optical analysis cell by a second rotatable liquid filling unit when the second rotatable liquid filling unit and the optical analysis cell have rotated to a prescribed third filling position on the rotatable turntable.

7. The method of claim 1 wherein first dye solution has a red absorption wavelength component, and the second dye solution has a blue absorption wavelength component.

8. The method of claim 1 wherein the plurality of optical analysis cells are sequentially arranged along a peripheral edge of a rotatable turntable that rotates intermittently in a first direction.

9. The method of claim 8 wherein the first dye solution is provided into the optical analysis cell by a first rotatable liquid filling unit when the first rotatable liquid filling unit and the optical analysis cell has rotated to a prescribed first filling position on the rotatable turntable.

10. The method of claim 9 wherein the second dye solution by a diluent dispensing pipetter when the optical analysis cell containing the first dye solution has rotated to a prescribed second filling position on the rotatable turntable.

11. The method of claim 10 wherein measuring the weight of the second dye solution based on gravimetric method comprises:
    measuring the total weight of the diluent dispensing pipetter and the second dye solution contained therein to obtain a first weight measurement before providing the second dye solution into the optical analysis cell; and
    measuring the weight of the diluent dispensing pipetter to obtain a second weight measurement after providing the second dye solution into the optical analysis cell.

12. The method of claim 10 wherein the first optical analysis measurement on the target test liquid contained in the optical analysis cell is performed when the optical analysis cell has reached a prescribed measurement position on the rotatable turntable.

13. A method for validating the accuracy of automated analyzers comprising:
    providing a first dye solution which absorbs light of a first wavelength into one of a plurality of optical analysis cells;
    measuring the weight of a second dye solution which absorbs light of a second wavelength which is different from the first wavelength;
    providing the second dye solution into the optical analysis cell containing the first dye solution, wherein the first and second dye solutions form a target test liquid;
    performing a first optical measurement on the target test liquid contained in the optical analysis cell to obtain an amount of the first dye solution as a first measurement result;
    removing the target test liquid from the optical analysis cell and transferring the same target test liquid into a microplate which is separated and independent from the optical analysis cell;
    performing a second optical measurement based on the dye method on the same target test liquid contained in the microplate to obtain the amount of the first dye solution as a second measurement result; and
    validating the accuracy of the amount of the first dye solution by performing a computational analysis to determine any deviation between and among the first and second measurement results and the weight measurement of the second dye solution.

14. The method of claim 13 wherein the first and second optical measurements are performed based on a dye method.

* * * * *

UNITED STATES PATENT AND TRADEMARK OFFICE
CERTIFICATE OF CORRECTION

PATENT NO. : 8,928,884 B2  
APPLICATION NO. : 13/439861  
DATED : January 6, 2015  
INVENTOR(S) : Hattori et al.

Page 1 of 1

It is certified that error appears in the above-identified patent and that said Letters Patent is hereby corrected as shown below:

On the Title Page, item (12): "Hattori" should read -- Hattori et al. --.

On the Title Page, item (75): Add as co-inventors "George Rodrigues, Westbrook, ME; A. Bjoern Carle, Portland, ME"

Signed and Sealed this  
Fifteenth Day of March, 2016

Michelle K. Lee  
*Director of the United States Patent and Trademark Office*